United States Patent [19]

Suzuki et al.

[11] Patent Number: 4,877,447
[45] Date of Patent: Oct. 31, 1989

[54] METHOD AND COMPOSITION FOR INCREASING HARVESTS OF CROPS

[75] Inventors: Akinori Suzuki, Chiba; Toshio Kajita, Narashino; Masakazu Furushima, Nagareyama, all of Japan

[73] Assignee: Mitsubishi Gas Chemical Company, Inc., Tokyo, Japan

[21] Appl. No.: 71,257

[22] Filed: Jul. 8, 1987

[30] Foreign Application Priority Data

Jul. 11, 1986 [JP] Japan .................................. 61-161974

[51] Int. Cl.$^4$ ............................................. A01N 41/06
[52] U.S. Cl. ........................................... 71/103; 71/77; 71/79; 562/104
[58] Field of Search ............................. 71/103, 77, 79; 260/513 N

[56] References Cited

U.S. PATENT DOCUMENTS 3,712,803 1/1973 Grybek et al. .......................... 71/79

FOREIGN PATENT DOCUMENTS 0167559 9/1984 Japan ................................ 260/513 N
0061558 4/1985 Japan ................................ 260/513 N Primary Examiner—Richard L. Raymond
Assistant Examiner—Amelia A. Owens
Attorney, Agent, or Firm—Wenderoth, Lind & Ponack

[57] ABSTRACT

A method of increasing the harvest of a crop which comprises applying an effective amount of taurine to the crop or its seeds, and a composition therefor.

15 Claims, No Drawings

METHOD AND COMPOSITION FOR INCREASING HARVESTS OF CROPS

This invention relates to a method of increasing the harvest of a crop, and a composition therefor, and more specifically, it relates to a method of increasing the harvest of a crop using taurine, and a composition used therefor.

It is known that taurine is present in large quantities in bovine bile and flesh extracts of mollusks such as cuttlefish, octopus and shellfish. It has not been reported however that application of taurine to a crop results in an increased harvest.

Biologically, agricultural production is characterized by accumulating solar energy on the earth utilizing the photosynthesizing ability of green plants. At the same time, it supplies oxygen to the atmosphere. This is, however, not an entirely efficient method of utilizing solar energy. It is anticipated that the present world population will be nearly doubled at the end of this century. In view of the current food situation in the world, it will be extremely difficult to secure foods for the increased population.

Many research efforts have been made in the past to cope with the population increase. Many of the prior development works made to increase agricultural production resulted only in improvement of production technology, and little efforts have been undertaken to grasp, and strengthen, the particulars of the inherent functions of plants. Generally, plants utilize solar energy by their photosynthetic actions, whereby they synthesize carbohydrates from water and carbon dioxide and supply oxygen to the atmosphere.

The present inventors have made investigations on increasing the solar energy fixing function of green plants, and consequently found that by applying taurine to plants, the plants can perform photosynthesis more efficiently.

Accordingly, the present invention provides a method of increasing the harvest of a crop, which comprises applying an effective amount of taurine to the foliage or the roots of crops or their seeds.

Taurine can be applied in accordance with this invention in the same way as the application of ordinary agricultural chemicals. Preferably, it may be sprayed onto the foliage of crops, or crop seeds may be immersed in an aqueous solution of taurine.

The amount of taurine to be applied is not critical, but can be varied over a wide range depending upon the type of the crops, the growth stage of the crops, the method of application, the time of application, etc. Generally, when it is applied to a crop, the amount of taurine is 50 to 10,000 g, preferably 100 to 4,000 g, more preferably 200 to 2,000 g, per hectare (ha) of the locus where the crop is cultivated. In the immersion treatment of seeds, the seeds may suitably be immersed in an aqueous solution containing taurine in a concentration of 0.1 to 10,000 ppm, preferably 0.3 to 1,000 ppm, more preferably 1 to 500 ppm.

The immersion treatment time is 1 to 48 hours, preferably 3 to 24 hours. The temperature at which the immersion treatment is carried out is not particularly restricted, and is preferably room temperature.

The time of applying taurine is not particularly restricted, and can be varied according to the type of the crop. Generally, it is preferably applied when photosynthesis of the plant is vigorous, for example, at any desired stage from the reproductive growth period to the harvesting period. Depending upon the crop, better results may be obtained when it is used in the vegetative growth period. The optimum time of application is conveniently determined by performing a small scale experiment for every particular plant to which taurine is to be applied.

Taurine used in the method of this invention is a compound represented by the formula $H_2N-CH_2-CH_2-SO_3H$. Since it has the basic amino group and the acidic s acid group, it can form a salt both with an acid and an alkali. Taurine is weakly acidic, and is preferably used after neutralization with an alkali such as sodium hydroxide or potassium hydroxide.

There is no particular limitation on the crop whose increased harvest can be expected in accordance with the method of this invention. Plants which are important supply sources of foods are preferred. Specifically, for example, taurine used in this invention can promote the root formation of plants such as rice, wheat, barley, beet, sweet potato, potato, onion, corn and sugarcane, nurse their sound seedlings, promote their growth in the early stage, and increase the harvest of the crops. Furthermore, it can increase the sweetness and size of fruits such as apple, persimmon, peach, orange and lemon, promote their coloration, and maintain their freshness. Particularly, the method of this invention can be advantageously applied for the promotion of root formation in soybean and rice plants and consequently increase the harvest of these crops.

The method of this invention can markedly increase the qualitative and quantitative harvests of these crops.

For application to plants and their seeds in accordance with the method of this invention, taurine is desirably formulated into forms suitable for application.

Thus, the present invention also provides a composition comprising an effective amount of taurine and an agriculturally and horticulturally acceptable carrier or diluent.

The composition may be in formulations similar to ordinary agricultural chemicals, such as a dust, granules, a wettable powder, emulsifiable concentrates, an aqueous solution, an emulsion, an aqueous suspension, or an oily suspension. Depending upon the type of formulation, the composition may generally contain 0.5 to 90% by weight, preferably 1 to 80% by weight, of taurine.

The agriculturally and horticulturally acceptable carrier or diluent may be any of those which are known in the field of agricultural chemicals. For example, it may be selected from water, talc, bentonite and clay.

Particularly preferably, the composition of this invention is sprayed onto the foliage of crops in the form of an aqueous solution The concentration of taurine in the aqueous solution is generally 100 to 20,000 ppm, preferably 200 to 15,000 ppm, more preferably 300 to 10,000 ppm. In order to permit easy adhesion and penetration of taurine to and into the crops, the aqueous solution may further include a surface-active agent as a spreader. Examples of such a surface-active agent include nonionic surface-active agents such as alkyl phenol polyethylene glycols, polyoxyethylene alkyl aryl ethers and polyoxyethylene alkylphenyl ethers, anionic surface-active agents such as ligninsulfonic acid, and cationic surface-active agents such as aliphatic quaternary ammonium salts. They may be used either singly or in combination.

As required, the composition of this invention may further include other agriculturally active components such as fertilizers, insecticides, fungicides, nematocides, acaricides and plant growth regulators. It may also be mixed as required with a surface-spraying fertilizer such as urea, potassium phosphate or magnesium sulfate.

The following examples illustrate the present invention more specifically.

Taurine used in these examples was an extra pure grade made by Wako Pure Chemicals Industry Co., Ltd.

EXAMPLE 1

Wheat (Norin # 61) was cultivated for 10 days in vermiculite as soil in a phytotron under natural light which was maintained at 25° C. in the daytime and 20° C. at night. Protoplasts and complete chloroplasts were isolated from the wheat by conventional methods. The effect of taurine on the photosynthesis of the protoplasts and the complete chloroplasts was examined by using an oxygen electrode.

Specifically, light of 100,000 luxes was irradiated at 25° C. in the presence of 10 mM $NaHCO_3$, and the photosynthesizing abilities of the protoplasts and the complete chloroplasts were examined from the rates of oxygen released by them.

The protoplasts or the complete chloroplasts were incubated for 1 minute in a reaction solution consisting of 50 mM HEPES-KOH (PH 7.6), 0.4 M sorbitol and 1 mM EDTA. Then, light was irradiated to start photosynthesis. The results are shown in Table 1 in which the photosynthesizing ability of the non-treated area is taken as 100.

TABLE 1

| Taurine | Protoplasts | Chloroplasts |
| --- | --- | --- |
| Non-treated | 100 | 100 |
| 0.01 mM | 109 | 110 |

EXAMPLE 2

Rice plants (variety: "nihonbare") were transferred to Wagner pots (1/5000 a) filled with paddy soil and cultivated outdoors. Sixty days later, an aqueous solution of taurine containing 0.2% of Lino (trade name) as a surfactant, (20.0% of alkylphenol polyethylene glycol and 12.0% of ligninsulfonate) was sprayed on the foliage of the rice plants in each of the dosages shown in Table 2 at a rate of 10 liters/a. After 120 days, the harvest was examined. The results are shown in Table 2.

As a base fertilizer, 0.4 g of N, 0.8 g of P and 0.8 g of K were used per pot, and 65 days after the start of the cultivation, 0.2 g of N was additionally applied.

In the present test, 7 pots were used in each area, and the average of the measured values obtained in the 7 pots was determined. It is seen that the harvest increased as compared with the non-treated area.

TABLE 2

| Dosages (g/ha) | Harvest as the ratio to the non-treated area | | |
| --- | --- | --- | --- |
| | Plant height | Number of ears | Weight of mulled rice |
| Non-treated | 100 (81.9 cm) | 100 (5.8) | 100 (13.3 g) |
| Taurine (1000) | 103 | 102 | 144 |
| Taurine | 103 | 102 | 127 |

TABLE 2-continued

| Dosages (g/ha) | Harvest as the ratio to the non-treated area | | |
| --- | --- | --- | --- |
| | Plant height | Number of ears | Weight of mulled rice |
| (300) | | | |

EXAMPLE 3

Seeds of soybean (variety: "suzuyutaka") were immersed for 24 hours in an aqueous solution of taurine in a concentration of 0.1 ppm, 10 ppm, 100 ppm, and 1000 ppm respectively. The immersed seeds were washed with water and sown in pots (1/500 a ) filled with upland farm soil at a rate of three per pot. There were cultivated in a greenhouse, and their growth was examined 66 days later. The test results are shown in Table 3.

TABLE 3

| Concentration (ppm) | Dry weight as the ratio to one immersed in water alone | | | |
| --- | --- | --- | --- | --- |
| | Leaf portion | Stalk portion | Root portion | Young pad |
| 0 (water alone) | 100 (2.6 g/ plant) | 100 (0.9 g/ plant) | 100 (0.77 g/ plant) | 100 (0.3 g/ plant) |
| 1 | 112 | 100 | 104 | 133 |
| 10 | 135 | 122 | 117 | 167 |
| 100 | 127 | 122 | 130 | 133 |
| 1000 | 123 | 100 | 139 | 100 |

EXAMPLE 4

Forcedly germinated rice seeds (variety: "nihonbare") were sown in 75 ml of 0.7% agar medium containing taurine in each of the concentrations indicated in Table 4 at a rate of five seeds in a beaker having an inside diameter of 4 cm and a depth of 7.5 cm.

They were grown for 13 days in a phytotron kept at 25° C. in the daytime and 20° C. at night and irradiated at an illuminance of about 28 kiloluxes for 12 hours a day. The dry weights of the aboveground portion and the root portion were measured. The results are shown in Table 4.

TABLE 4

| Concentration (ppm) | Dry weight of the foliage portion as the ratio to the non-treated area | Dry weight of the root portion as the ratio to the non-treated area |
| --- | --- | --- |
| 0.1 | 105 | 113 |
| 1 | 109 | 124 |
| 10 | 118 | 116 |
| Non-treated | 100 (45 mg/5 plants) | 100 (15 mg/5 plants) |

EXAMPLE 5

On May 8, young rice seedlings (variety: "koshihikari") were transplanted in a paddy by a machine in a customary manner. Forty days before earing, the paddy was divided into areas each having an area of 5 $m^2$. Granules containing taurine and prepared as in Formulation Example 3 below were scattered by hand in each of the dosages shown in Table 5. The length of the culm was examined 20 days after earing, and 30 days after earing, the harvest was examined.

The results are shown in Table 5.

TABLE 5

| Chemical | Dosage (g/ha) | Culm length as the ratio to the non-treated area | Harvest as the ratio to the non-treated area |
| --- | --- | --- | --- |
| Taurine | 600 | 95 | 120 |
|  | 1200 | 95 | 135 |
| Non-treated area | — | 100 | 100 |

FORMULATION EXAMPLE 1

Aqueous solution:

Thirty grams of taurine are dissolved by adding 100 g of water, and while the pH of the solution is measured by a pH meter, a 5N aqueous solution of sodium hydroxide is added to adjust the pH of the solution to 7.0. Five 9rams of polyoxyethylene oleyl ether and 5 g of triethanolamine lauryl sulfate are added. Water is further added to adjust the total amount of the aqueous solution to 300 g. This solution contains 10% of taurine. Usually, it is applied after being diluted with water to 50 to 1000 times.

FORMULATION EXAMPLE 2

Wettable powder:

Fifty grams of taurine, 2 g of sodium dodecylbenzenesulfonate, 1 g of polyoxyethylene alkyl aryl ether, 10 g of talc and 37 g of bentonite are uniformly mixed and pulverized to give a wettable powder containing 50% of taurine.

FORMULATION EXAMPLE 3

Granules:

Fifty grams of taurine, 475 g of bentonite and 475 g of diatomaceous earth are uniformly mixed. The uniform mixture is finely pulverized and granulated in a customary manner to form granules.

What we claim is:

1. A method of increasing the harvest of a crop which comprises applying 50 to 10,000 g of taurine per hectare at the locus where the crop is cultivated.
2. A method of increasing the harvest of a crop which comprises applying 100 to 4,000 g of taurine per hectare at the locus where the crop is cultivated.
3. A method of increasing the harvest of a crop which comprises immersing the seeds of a crop in an aqueous solution of taurine.
4. The method of claim 3 wherein the crop is selected from rice, wheat, barley, beet, sweet potato, potato, onion, corn, sugarcane, apple, persimmon, peach, orange and lemon.
5. The method of claim 1 wherein taurine is applied to the foliage portion or the root portion of the crop.
6. The method of claim 3 wherein the concentration of taurine in the aqueous solution is 0.1 to 10,000 ppm.
7. The method of claim 6 wherein the concentration of taurine in the aqueous solution is 0.3 to 1,000 ppm.
8. The method of claim 1 wherein taurine is applied in a stage between the reproductive growth period to the harvesting period of the crop.
9. The method of claim 1 wherein the crop is selected from rice, wheat, barley, beet, sweet potato, potato, onion, corn, sugarcane, apple, persimmon, peach, orange and lemon.
10. A composition useful for increasing the harvest of a crop, comprising an effective amount of taurine or its alkali neutralization product and a carrier or diluent.
11. The composition of claim 10 which is in the form of a dust, granules, a wettable powder, an emulsifiable concentrate, an aqueous solution, an emulsion, an aqueous suspension, or an oil suspension.
12. The composition of claim 10 which contains taurine in a concentration of 0.5 to 90% by weight.
13. The composition of claim 10 which is in the form of an aqueous solution.
14. The composition of claim 13 which contains taurine in a concentration of 100 to 20,000 ppm.
15. The composition of claim 13 which further comprises a surface-active agent.

* * * * *